United States Patent
Ernst et al.

(10) Patent No.: US 8,492,579 B2
(45) Date of Patent: Jul. 23, 2013

(54) METHOD FOR PRODUCING ASTAXANTHIN DIMETHYLDISUCCINATE

(75) Inventors: Hansgeorg Ernst, Speyer (DE); Walter Dobler, Schwetzingen (DE); Andreas Keller, Speyer (DE); Klaus Henrich, Haβloch (DE)

(73) Assignee: BASF SE (DE)

( * ) Notice: Subject to any disclaimer, the term of this patent is extended or adjusted under 35 U.S.C. 154(b) by 351 days.

(21) Appl. No.: 13/021,173

(22) Filed: Feb. 4, 2011

(65) Prior Publication Data

US 2011/0196170 A1 Aug. 11, 2011

Related U.S. Application Data

(60) Provisional application No. 61/302,183, filed on Feb. 8, 2010.

(51) Int. Cl.
*C07C 403/24* (2006.01)
(52) U.S. Cl.
USPC .......................... 560/194; 560/193; 560/190
(58) Field of Classification Search
None
See application file for complete search history.

(56) References Cited

U.S. PATENT DOCUMENTS

2007/0110881 A1\* 5/2007 Gloor et al. ................. 426/635

FOREIGN PATENT DOCUMENTS

| WO | WO-03/066583 A1 | 8/2003 |
| WO | WO-2007/128574 A1 | 11/2007 |

OTHER PUBLICATIONS

Widmer et al., "Technische Verfahren zur Synthese von Carotinoiden und verwandten Verbindungen aus 6-Oxo-isophoron", Helvetica Chimica Acta, vol. 64, Fasc. 7, pp. 2436-2446, 1981.

\* cited by examiner

*Primary Examiner* — Yevegeny Valenrod
(74) *Attorney, Agent, or Firm* — Novak Druce Connolly Bove + Quigg LLP

(57) ABSTRACT

The present invention relates to an improved method for producing all-E astaxanthin dimethyldisuccinate of the formula I.

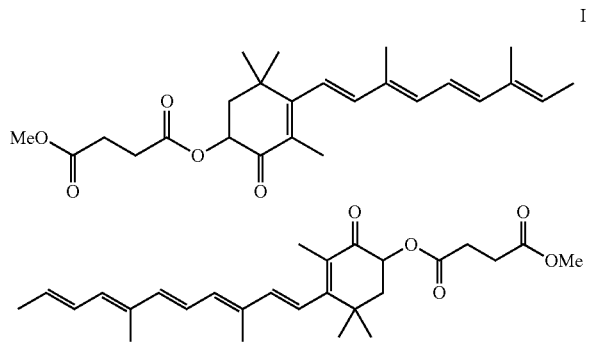

7 Claims, No Drawings

METHOD FOR PRODUCING ASTAXANTHIN DIMETHYLDISUCCINATE

CROSS-REFERENCE TO RELATED APPLICATIONS

This application claims benefit of U.S. Provisional application 61/302,183, filed Feb. 8, 2010.

BACKGROUND OF THE INVENTION

The present invention relates to an improved method for producing all-E astaxanthin dimethyldisuccinate of the formula I.

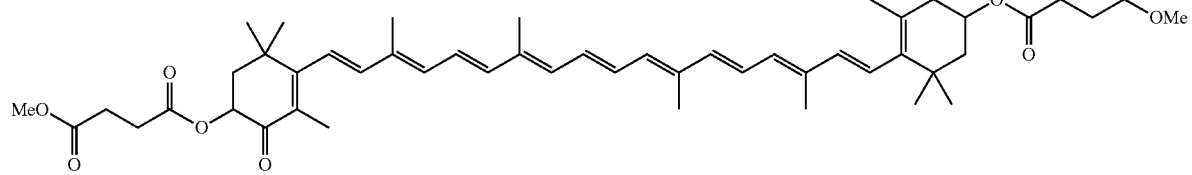

Astaxanthin itself is a sought-after dye which is used primarily as a feed additive for pigmenting farmed salmon.

A very efficient method for producing astaxanthin is the double Wittig olefination of the symmetrical $C_{10}$ dialdehyde of the formula II with two equivalents of the corresponding 015 phosphonium salt of the formula III as described, inter alia, in Helv. Chim. Acta 64, 7, 2445 (1981).

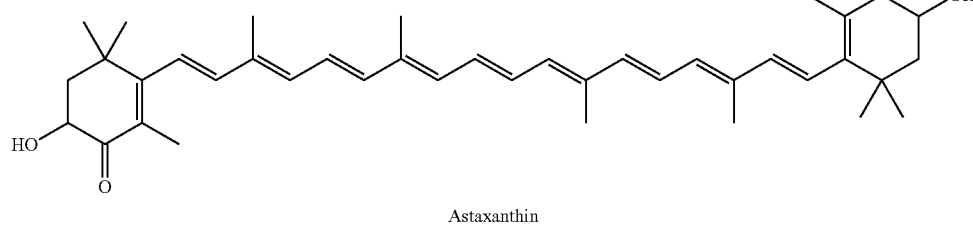

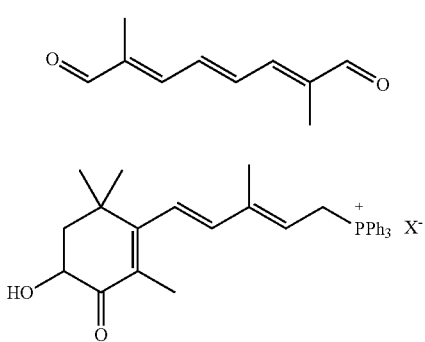

This reaction can be carried out, for example in dichloromethane using methanolic sodium methoxide solution as base (cf. also WO 2007128574) or by heating the components of the formulae II and III in 1,2-epoxybutane.

For improving the storage stability of astaxanthin in fish food, various diesters of astaxanthin are proposed in WO 03/066583, wherein, inter alia, astaxanthin dimethyldisuccinate of the formula I is mentioned.

For producing the diesters of astaxanthin, according to WO 03/066583, crystalline astaxanthin is reacted in an inert solvent with a carboxylic acid chloride or a carboxylic acid anhydride in the presence of an organic base (WO 03/066583, page 7, lines 3 to 20). In the esterification of astaxanthin with a free acid, the reaction proceeds in the presence of a dehydrating reagent (WO 03/066583, page 7, lines 21 to 28).

Astaxanthin dimethyldisuccinate of the formula I was obtained according to example 5 in WO 03/066583 (page 13, lines 13 to 25) in a yield of 49.9% and a purity of 79.3%. By subsequent recrystallization from methylene chloride/methanol, the diesters could be obtained in a purity of 98% (after HPLC).

A disadvantage of this procedure is that the starting material used for the esterification is crystalline astaxanthin. The production of crystalline astaxanthin as an intermediate for the esterification means considerable production expenditure for crystallization, filtration, washing, drying, packaging, storage and metering the solid in the subsequent stage. In addition, in the crystallization of astaxanthin, losses of yield occur owing to the residual solubility of the product of value in the mother liquor.

BRIEF SUMMARY OF THE INVENTION

It was an object of the present invention to improve the disadvantages of the known synthesis of astaxanthin dimethyldisuccinate of the formula I. The method for producing astaxanthin dimethyldisuccinate of the formula I should be simplified, and the yield and purity of astaxanthin dimethyldisuccinate of the formula I should be improved.

This object is achieved by a method for producing all-E astaxanthin dimethyl-disuccinate of the formula I

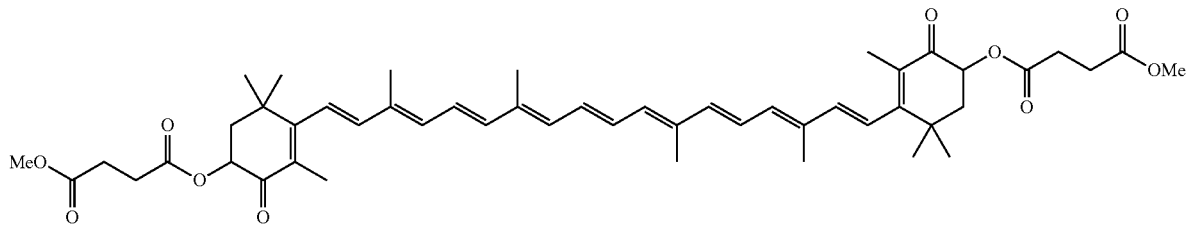

which comprises the process steps:

a) reacting a $C_{10}$ dialdehyde of the formula II

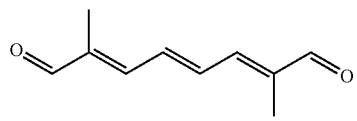

in a double Wittig reaction with a $C_{15}$ phosphonium salt of the formula III

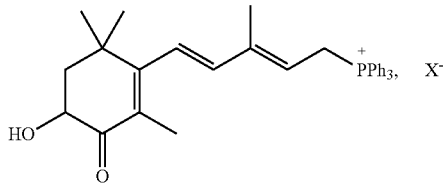

where $X^-$ is the anion of an organic or inorganic acid HX, in a solvent comprising dichloromethane by adding a solution of an alkali metal alkoxide or alkaline earth metal alkoxide $M^1OR^1$ or $M^2(OR^1)_2$ in an alcohol $R^1OH$ as base, where $M^1$ is Li, Na, K or Rb, $M^2$ is Mg, Ca, Sr or Ba and $R^1$ is methyl, ethyl, n-propyl or isopropyl, to give an astaxanthin of the formula IV

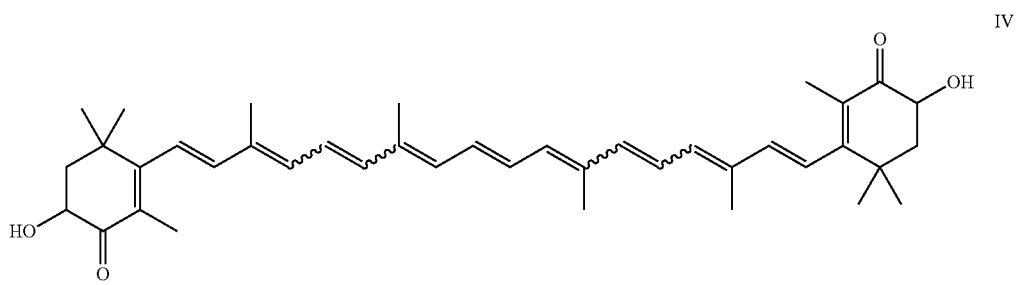 [SMILES: CC(C=CC=C(C)/C=C/C1=C(C)C(=O)C(O)CC1(C)C)=C/C=C/C=C(C)C=CC=C(C)/C=C/C1=C(C)C(=O)C(O)CC1(C)C]

wherein the two new double bonds formed are not only present in the Z configuration but also in the E configuration,
optionally followed by an aqueous workup of the reaction mixture for removing the salts M¹X or M²X₂;
b) removing the alcohol R¹OH from the reaction mixture of process step a) by repeated washing of the reaction mixture with water or by distilling off a solvent mixture comprising dichloromethane and the alcohol R¹OH,
optionally followed by drying the reaction mixture by removing water by means of azeotropic distillation of dichloromethane and water;
c) reacting the astaxanthin of the formula IV which is present in the reaction mixture treated in process step b) in dichloromethane by adding methyl succinoyl chloride of the formula V

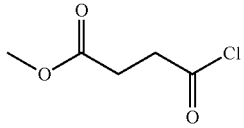

and an organic nitrogenous base to form an astaxanthin dimethyldisuccinate of the formula Ia:

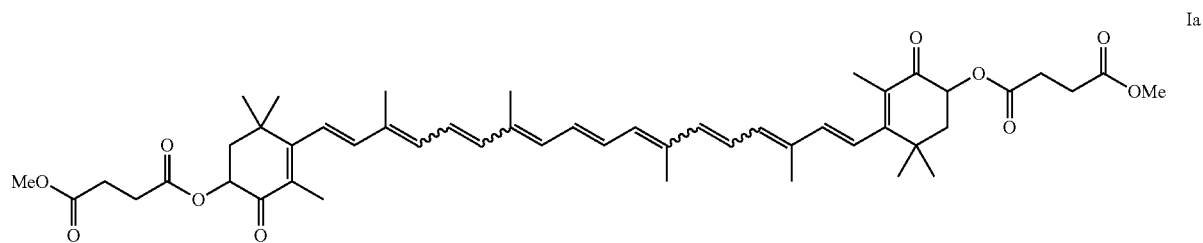 [SMILES: COC(=O)CCC(=O)OC1CC(C)(C)C(/C=C/C(C)=CC=CC(C)=C/C=C/C=C(C)C=CC=C(C)/C=C/C2=C(C)C(=O)C(OC(=O)CCC(=O)OC)CC2(C)C)=C(C)C1=O]

d) an aqueous workup of the reaction mixture of process step c) for removing water-soluble salts;
e) solvent exchange of dichloromethane by an alcohol R²OH by removing the dichloromethane from the reaction mixture of process step d) by distillation and adding the alcohol R²OH to the reaction mixture, wherein R² is methyl, ethyl, n-propyl or isopropyl;
f) thermal isomerization of the astaxanthin dimethyldisuccinate of the formula Ia produced in process step c) to give the all-E astaxanthin dimethyldisuccinate of the formula I by heating the R²OH-comprising reaction mixture of process step e) to at least 50° C., wherein the reaction mixture has a water content of 10 to 90% by volume of water based on the total volume of the reaction mixture, and wherein the all-E astaxanthin dimethyldisuccinate of the formula I occurs in crystalline form and is subsequently optionally isolated.

DETAILED DESCRIPTION OF THE INVENTION

In process step a) of the method according to the invention, a $C_{10}$ dialdehyde of the formula II

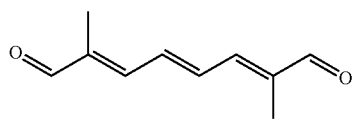

is reacted in a double Wittig reaction with a $C_{15}$ phosphonium salt of the formula III

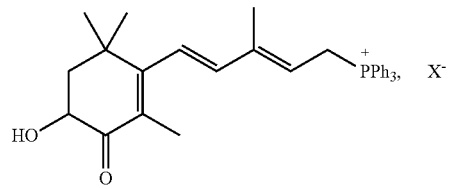

where X⁻ is the anion of an organic or inorganic acid HX, such as, for example hydrogen chloride, hydrogen bromide or hydrogen iodide, a sulfonic acid such as methanesulfonic acid, p-toluenesulfonic acid or trifluoromethanesulfonic acid, or a trihaloacetic acid, such as trifluoroacetic acid or trichloroacetic acid, in a solvent comprising dichloromethane by adding a solution of an alkali metal alkoxide or alkaline earth metal alkoxide M¹OR¹ or M²(OR¹)₂, preferably an alkali metal alkoxide M¹OR¹, in an alcohol R¹OH as base, where M¹ is Li, Na, K or Rb, preferably Li or Na, in particular Na, M² is Mg, Ca, Sr or Ba, preferably Mg and R¹ is methyl, ethyl, n-propyl or isopropyl, preferably methyl or ethyl, in particular methyl, to give an astaxanthin of the formula IV

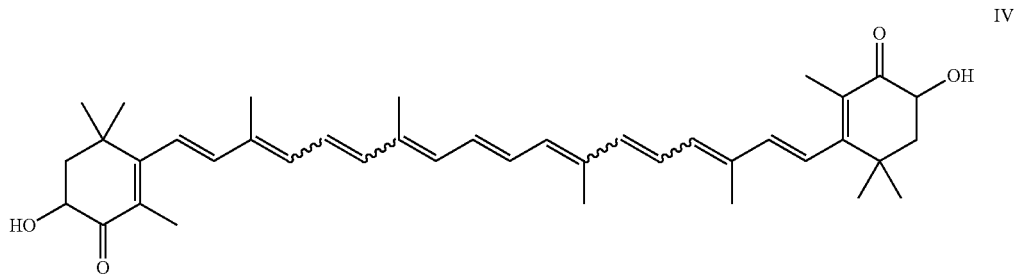 [SMILES: CC(C=CC=C(C)/C=C/C1=C(C)C(=O)C(O)CC1(C)C)=C/C=C/C=C(C)C=CC=C(C)/C=C/C1=C(C)C(=O)C(O)CC1(C)C]

wherein the two new double bonds formed are not only present in the Z configuration but also in the E configuration, optionally followed by an aqueous workup of the reaction mixture for removing the salts $M^1X$ or $M^2X_2$.

Preferably, the anion $X^-$ is chloride or bromide.

In process step a), preferably the $C_{10}$ dialdehyde of the formula II and the $C_{15}$ phosphonium salt of the formula III are first dissolved in a solvent comprising more than 90% by volume, particularly preferably more than 95% by volume, of dichloromethane based on the total volume of the solvent, in particular in pure dichloromethane, that is dichloromethane having a purity of greater than 99% by volume.

Subsequently, in process step a), the compounds of the formulae II and III are preferably condensed by adding a solution of sodium methoxide in methanol as base to give the astaxanthin of the formula IV.

In the astaxanthin of the formula IV the two newly formed double bonds are present not only in the Z configuration but also in the E configuration. Predominantly, that is to say at more than 50%, the two newly formed double bonds in the astaxanthin of the formula IV have the E, E configuration. The fraction of the newly formed double bonds having Z configuration is up to 25% in the mixture of the astaxanthin of the formula IV.

Preferably, in process step a), the reaction mixture is subjected to an aqueous workup for removing the salts $M^1X$ or $M^2X_2$.

After the aqueous workup, the reaction mixture obtained is a crude solution of astaxanthin of the formula IV in dichloromethane which is water-saturated and comprises residues of the alcohol $R^1OH$, in particular methanol.

In process step b) of the method according to the invention, the alcohol $R^1OH$ is removed from the reaction mixture of process step a) by repeated washing of the reaction mixture with water or by distilling off a solvent mixture comprising dichloromethane and the alcohol $R^1OH$, in particular by distilling off the solvent mixture comprising dichloromethane and the alcohol $R^1OH$, optionally followed by drying the reaction mixture by removing water by means of azeotropic distillation of dichloromethane and water.

Preferably, in process step b), the alcohol $R^1OH$, in particular methanol, is removed by repeated distillation, washing the distillate with water, and recycling the washed distillate into the crude astaxanthin solution.

In the case of methanol, the methanol can be removed from the reaction mixture as described hereinbefore discontinuously in a plurality of stages. In an industrial method, the removal of the methanol from the reaction mixture is preferably carried out continuously by removing the methanol from the reaction mixture by continuous washing of the methanol-comprising dichloromethane distillate with water in a mixer/settler apparatus. In this case the organic lower phase is recirculated continuously to the crude astaxanthin solution until the crude astaxanthin solution is methanol-free.

Preferably, after the methanol removal is completed, the water-saturated crude astaxanthin solution is dried by methods known to those skilled in the art, preferably by azeotropic distillation (dichloromethane/water heteroazeotrope). This can be performed by simple partial vaporization or by purging water by means of an appropriately constructed water separator.

All distillation steps are preferably carried out at atmospheric pressure, but can also take place under reduced pressure. For practical reasons (condensability of the dichloromethane azeotrope), however, pressures below 300 mbar are not employed.

In process step c) of the method according to the invention, the astaxanthin of the formula IV which is present in the reaction mixture treated in process step b) is reacted in dichloromethane by adding methyl succinoyl chloride of the formula V

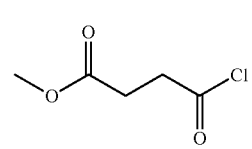

and an organic nitrogenous base to form an astaxanthin dimethyldisuccinate of the formula Ia

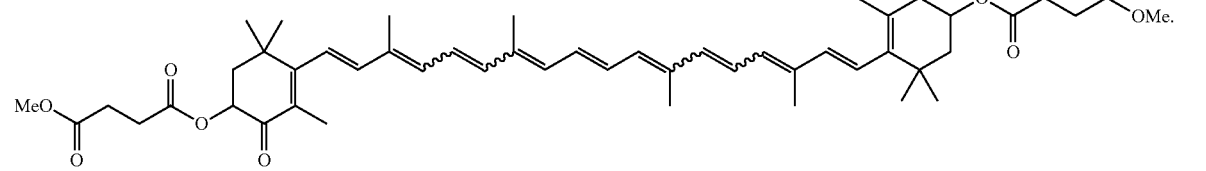

The $R^1OH$-free, preferably also water-free, in particular methanol- and water-free dichloromethane solution of crude astaxanthin which is obtained in process step b) is reacted in a manner known per se with the methylsuccinoyl chloride of the formula V in the presence of an organic base to give the astaxanthin dimethyldisuccinate of the formula Ia. Water-free or $R^1OH$-free in this context means a water content or an $R^1OH$ content in the reaction mixture of less than 0.2% by weight, preferably less than 0.1% by weight, in particular less than 0.075% by weight, of water or of $R^1OH$, based on the mass of the reaction mixture.

As organic, nitrogenous base, use can be made of, for example, amines such as primary, secondary or tertiary alkylamines or arylamines, or basic nitrogenous heteroaromatics such as pyridine or pyridine derivatives. Preferably, the base used is a trialkylamine such as for instance triethylamine, pyridine or a dialkylaminopyridine such as, for instance, 4-dimethylaminopyridine. Particularly preferably, in process step c), the organic nitrogenous base is pyridine or a pyridine derivative.

The molar ratio of astaxanthin:methylsuccinoyl chloride is in the range of 1:2.0-1:3.0, preferably 1:2.1-1:2.5. The base is used at least stoichiometrically to the acid chloride, but preferably in an excess of 10-50 mol %, based on methylsuccinoyl chloride. The reaction temperature can be from $-10°$ C. up to the reflux temperature of the reaction mixture. Preferably, the reaction is carried out in the temperature range from 0 to 25° C.

In process step d) of the method according to the invention, the reaction mixture of method step c) is worked up under aqueous conditions for removing water-soluble salts. In this process the hydrochlorides of the organic nitrogenous base are substantially removed from the dichloromethane-comprising reaction mixture, and also any salts $M^1X$ or $M^2X_2$ which are still present and were formed in process step a).

In process step e) of the method according to the invention, the solvent dichloromethane is exchanged for an alcohol $R^2OH$ by removing the dichloromethane from the reaction mixture of process step d) by means of distillation and addition of the alcohol $R^2OH$ to the reaction mixture, wherein $R^2$ is methyl, ethyl, n-propyl or isopropyl, in particular is methyl.

Preferably, in process step e), the alcohol $R^2OH$ is methanol.

The solvent exchange can be performed stepwise, by distilling off a certain amount of dichloromethane and replacing it with a certain amount of alcohol $R^2OH$ and repeating this procedure until the dichloromethane has been removed in the desired amount, preferably completely. Alternatively, the dichloromethane which is removed by distillation can also be continuously replaced by the corresponding volume of the alcohol $R^2OH$ (isochoric procedure). Complete removal of dichloromethane means, in the above context, that the residual content of dichloromethane is less than 0.5% by weight, preferably less than 0.1% by weight, in particular less than 0.05% by weight of dichloromethane, based on the mass of the reaction mixture.

The solvent exchange is performed in order to be able to crystallize out the astaxanthin dimethyldisuccinate of the formula Ia and, in particular, the all-E astaxanthin dimethyldisuccinate of the formula I which are readily soluble in dichloromethane from an alcohol $R^2OH$, wherein the triphenylphosphine oxide from process step a) which is still present remains in solution and therefore can readily be separated off from the crystalline product.

Preferably, water is added to the alcohol $R^2OH$, in particular methanol, wherein the amount of water is selected such that the triphenylphosphine oxide does not yet precipitate out.

In principle the water can have been added to the reaction mixture, at least in part, even before the solvent exchange (process step e)). For simpler calculation and determination of the required amount of water for a desired water content, the water is not added to the reaction mixture until after the solvent exchange of dichloromethane for the alcohol $R^2OH$, in particular methanol. Preferably, a water content of 10 to 90% by volume, particularly preferably 30 to 70% by volume, very particularly preferably 40 to 60% by volume, in particular 45 to 55% by volume, based on the total volume of the reaction mixture, is set.

In process step f) of the method according to the invention, the astaxanthin dimethyldisuccinate of the formula Ia which is produced in process step c) is thermally isomerized to give the all-E astaxanthin dimethyldisuccinate of the formula I by heating the $R^2OH$-comprising reaction mixture from process step e) to at least 50° C., wherein the reaction mixture has a water content of 10 to 90% by volume, particularly preferably 30 to 70% by volume, very particularly preferably 40 to 60% by volume, in particular 45 to 55% by volume of water, based on the total volume of the reaction mixture, and wherein the all-E astaxanthin dimethyldisuccinate of the formula I occurs in crystalline form and is subsequently optionally isolated.

The reaction mixture from process step e) is preferably isomerized at a temperature between 80 and 120° C., particularly preferably between 90 and 110° C. If the desired temperature is above the boiling point of the solvent or of the solvent mixture at atmospheric pressure, the reaction mixture is heated in a closed system which is suitable for the overpressure which builds up.

Preferably, in process step f), the thermal isomerization is carried out in aqueous methanol between 80 and 120° C., particularly preferably between 90 and 110° C., under the inherent pressure in a closed apparatus.

The reaction mixture is customarily thermally isomerized for 1 to 20 h at a temperature between 80 and 120° C. At lower temperatures this time can also be longer.

Preferably, the water content defined in process step f) is set by adding water to the reaction mixture subsequently to process step e).

After the thermal isomerization, the mixture is customarily cooled to 0 to 25° C., preferably 0 to 12° C., and the all-E astaxanthin dimethyldisuccinate of the formula I which has crystallized out can be isolated in high yield and purity by filtration.

The above-described method according to the invention avoids the disadvantages of the two-stage process in which, first all-E astaxanthin is isolated and this crystalline product is then converted to the all-E astaxanthin dimethyldisuccinate of the formula I. Surprisingly it has been found that an astaxanthin of the formula IV which is produced from the $C_{10}$ dialdehyde of the formula II and the $C_{15}$ phosphonium salt of the formula III, for the conversion into astaxanthin dimethyldisuccinate of the formula Ia, need not be isolated so as to be solvent free, but can be reacted directly with methylsuccinoyl chloride of the formula V (methyl 4-chloro-4-oxobutyrate) as a crude solution in the presence of triphenylphosphine oxide and other impurities from the synthesis to give astaxanthin dimethyldisuccinate of the formula Ia and, therefrom, after thermal isomerization, all-E astaxanthin dimethyldisuccinate of the formula I can be obtained in crystalline form in high yield and purity.

The invention will be described by the following example which is not limiting, however.

Example 1

The crude astaxanthin solution was produced by reacting II with III in dichloromethane using methanolic sodium methoxide solution (cf. Helv. Chim. Acta 64, 7, 2445 (1981)). The solution comprised 4.56% by weight of astaxanthin (HPLC analysis) and 0.8% by weight of methanol (GC analysis) and also 0.55% by weight of water (Karl-Fischer titration).

982 g of this solution (equivalent to 75 mmol of astaxanthin) were charged. At atmospheric pressure, 350 ml of solvent were distilled off over a Normag column head. The aqueous upper phase of the distillate was separated off and the lower phase was washed with 175 g of water. The phases were separated and the organic lower phase was recirculated to the distillation bottom.

This procedure was repeated further twice. Subsequently, 350 ml of solvent were distilled off at atmospheric pressure. The remaining distillation residue no longer comprised methanol. The water content was 0.051% by weight.

At 20° C., 21.36 g (270 mmol) of pyridine were added to the distillation residue. Subsequently, at 20° C., 34.92 g (225.0 mmol) of methylsuccinoyl chloride (methyl 4-chloro-4-oxobutyrate) were added dropwise in the course of 30 min. The reaction mixture was further stirred for 3 h at 20-25° C. Then, the reaction mixture was hydrolyzed by adding 100 ml of water. The aqueous phase was separated off and the organic phase was washed twice each time with 100 ml of water. Subsequently dichloromethane was distilled off via a Normag column head. The distillate was replaced simultaneously by methanol (isochoric procedure) until the transfer temperature had reached 65° C. The mixture was admixed with 300 ml of water, further stirred for 4 h at 100° C. under inherent pressure, cooled to 10° C. and extracted by stirring for 1 h at 10° C. The precipitated product was filtered off, washed twice each time with 50 ml of cold (10° C.) methanol and dried overnight in a vacuum drying cabinet at 50° C. at up to 10 mbar.

Sample weight: 52.5 g of Ax-DMDS (84.9% based on astaxanthin in the crude solution)
m.p.: 115-117° C.
Purity: 94.6% (HPLC area %)

The invention claimed is:
1. A method for producing all-E astaxanthin dimethyldisuccinate of the formula I

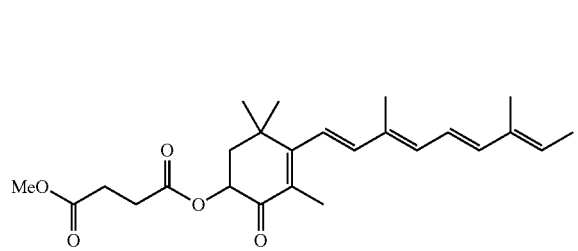
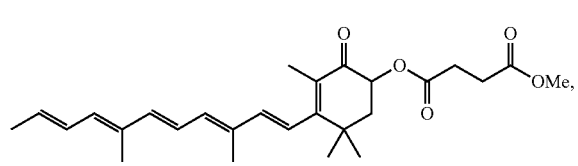

which comprises the process steps:
a) reacting a $C_{10}$ dialdehyde of the formula II

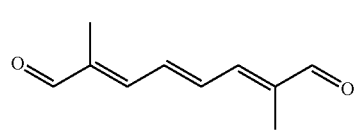

in a double Wittig reaction with a $C_{15}$ phosphonium salt of the formula III

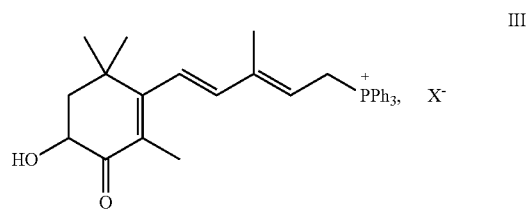

where $X^-$ is the anion of an organic or inorganic acid HX,
in a solvent comprising dichloromethane by adding a solution of an alkali metal alkoxide or alkaline earth metal alkoxide of the formulas $M^1OR^1$ or $M^2(OR^1)_2$ in an alcohol of the formula $R^1OH$ as base,
where
$M^1$ is Li, Na, K or Rb,
$M^2$ is Mg, Ca, Sr or Ba
and
$R^1$ is methyl, ethyl, n-propyl or isopropyl,
to give an astaxanthin of the formula IV

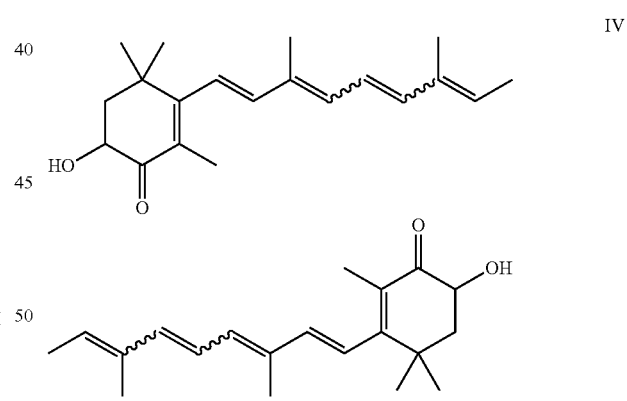

wherein the two new double bonds formed are not only present in the Z configuration but also in the E configuration,
optionally followed by an aqueous workup of the reaction mixture for removing the salts $M^1X$ or $M^2X_2$;
b) removing the alcohol $R^1OH$ from the reaction mixture of process step a) by repeated washing of the reaction mixture with water or by distilling off a solvent mixture comprising dichloromethane and the alcohol $R^1OH$,
optionally followed by drying the reaction mixture by removing water by means of azeotropic distillation of dichloromethane and water;

c) reacting the astaxanthin of the formula IV which is present in the reaction mixture treated in process step b) in dichloromethane by adding methyl succinoyl chloride of the formula V

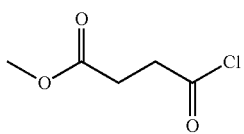

and an organic nitrogenous base to form an astaxanthin dimethyldisuccinate of the formula Ia;

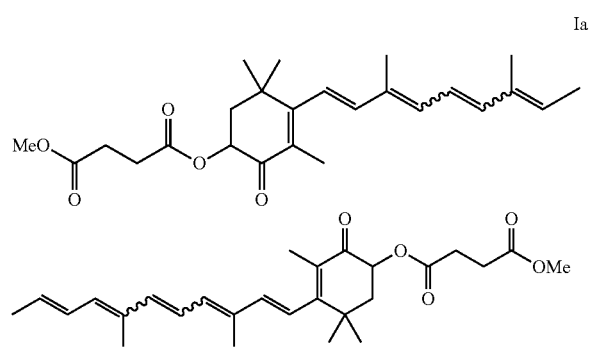

d) an aqueous workup of the reaction mixture of process step c) for removing water-soluble salts;

e) solvent exchange of dichloromethane by an alcohol $R^2OH$ by removing the dichloromethane from the reaction mixture of process step d) by distillation and adding the alcohol $R^2OH$ to the reaction mixture, wherein $R^2$ is methyl, ethyl, n-propyl or isopropyl;

f) thermal isomerization of the astaxanthin dimethyldisuccinate of the formula Ia produced in process step c) to give the all-E astaxanthin dimethyldisuccinate of the formula I by heating the $R^2OH$-comprising reaction mixture of process step e) to at least 50° C., wherein the reaction mixture has a water content of 10 to 90% by volume of water based on the total volume of the reaction mixture, and wherein the all-E astaxanthin dimethyldisuccinate of the formula I occurs in crystalline form and is subsequently optionally isolated.

2. The method according to claim 1, wherein, in process step a) the base is a solution of sodium methoxide in methanol.

3. The method according to claim 2, wherein, in process step b), the methanol is removed from the reaction mixture by continuous washing of the methanol-comprising dichloromethane distillate with water in a mixer/settler apparatus.

4. The method according to claim 1, wherein, in process step c), the organic nitrogenous base is pyridine or a pyridine derivative.

5. The method according to claim 1, wherein, in process step e), the alcohol $R^2OH$ is methanol.

6. The method according to claim 5, wherein, in process step f), the thermal isomerization is carried out in aqueous methanol between 80 and 120° C. under the inherent pressure in a closed apparatus.

7. The method according to claim 1, wherein the water content defined in process step f) is set by adding water to the reaction mixture subsequently to process step e).

* * * * *